(12) United States Patent
Proksa et al.

(10) Patent No.: US 9,316,601 B2
(45) Date of Patent: Apr. 19, 2016

(54) DETECTION VALUES PROCESSING APPARATUS

(75) Inventors: Roland Proksa, Neu Wulmstorf (DE); Gerhard Martens, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 188 days.

(21) Appl. No.: 13/981,610

(22) PCT Filed: Jan. 25, 2012

(86) PCT No.: PCT/IB2012/050344
§ 371 (c)(1),
(2), (4) Date: Jul. 25, 2013

(87) PCT Pub. No.: WO2012/104751
PCT Pub. Date: Aug. 9, 2012

(65) Prior Publication Data
US 2013/0308848 A1    Nov. 21, 2013

(30) Foreign Application Priority Data
Jan. 31, 2011    (EP) ..................................... 11152653

(51) Int. Cl.
*G01N 23/04*    (2006.01)
*A61B 6/03*    (2006.01)
(Continued)

(52) U.S. Cl.
CPC .............. *G01N 23/04* (2013.01); *A61B 6/032* (2013.01); *A61B 6/06* (2013.01); *A61B 6/4042* (2013.01);
(Continued)

(58) Field of Classification Search
None
See application file for complete search history.

(56) References Cited

U.S. PATENT DOCUMENTS 5,115,394 A * 5/1992 Walters .................... 382/131
6,973,158 B2   12/2005 Besson
(Continued)

FOREIGN PATENT DOCUMENTS

WO    2008107837 A1    9/2008
WO    2010004460 A1    1/2010
(Continued)

OTHER PUBLICATIONS

Schlomka, JP, et al. "Experimental feasibility of multi-energy photon-counting K-edge imaging in pre-clinical computed tomography." Physics in medicine and biology 53.15 (2008): 4031.*
(Continued)

*Primary Examiner* — Vikkram Bali
*Assistant Examiner* — Tracy Mangialaschi

(57) ABSTRACT

The invention relates to a detection values processing apparatus. Energy-dependent detection values are provided, which are indicative of polychromatic radiation (4) after having traversed an examination zone (5). The radiation is filtered by a filter (15) which comprises K-edge filter material. A component decomposition technique is applied to the detection values for determining K-edge attenuation values being first component attenuation values, which are indicative of an attenuation caused by the K-edge filter material, and additional component attenuation values, which are indicative of an attenuation caused by additional components of the examination zone, wherein an image of the examination zone is reconstructed from the additional component attenuation values. An image can therefore be reconstructed, which is not adversely affected by the filter, because the K-edge attenuation values are not used for reconstructing the image. This can improve the quality of the reconstructed image.

15 Claims, 4 Drawing Sheets

(51) Int. Cl.
*A61B 6/06* (2006.01)
*A61B 6/00* (2006.01)
*G06T 11/00* (2006.01)

(52) U.S. Cl.
CPC ............ *A61B 6/4241* (2013.01); *A61B 6/5205* (2013.01); *A61B 6/5258* (2013.01); *G01N 23/046* (2013.01); *G06T 11/003* (2013.01); *G01N 2223/419* (2013.01)

(56) References Cited

U.S. PATENT DOCUMENTS

| 2005/0089138 | A1* | 4/2005 | Toth et al. | 378/20 |
| 2009/0052621 | A1 | 2/2009 | Walter et al. | |
| 2009/0262997 | A1 | 10/2009 | Zou et al. | |
| 2010/0128948 | A1* | 5/2010 | Thomsen et al. | 382/131 |
| 2012/0076258 | A1* | 3/2012 | Chandra | A61B 6/03 378/5 |

FOREIGN PATENT DOCUMENTS

| WO | WO 2010004460 A1 * | 1/2010 |
| WO | WO 2010015953 A2 * | 2/2010 |
| WO | 2012042484 A1 | 4/2012 |
| WO | 2012077027 A1 | 6/2012 |

OTHER PUBLICATIONS

Llopart, X., et al.; First test measurements of a 64k pixel readout chip working in single photon counting mode; 2003; Nuclear Instruments and Methods in Physics Research; A 509:157-163.

Llopart, X., et al.; Medipix2: a 64-k Pixel Readout Chip with 55-um Square Elements Working in Single Photon Counting Mode; 2002; IEEE Trans. on Nuclear Science; 48(5)2279-2283.

* cited by examiner

DETECTION VALUES PROCESSING APPARATUS

FIELD OF THE INVENTION

The invention relates to a detection values processing apparatus, a detection values processing method and a detection values processing computer program. The invention relates further to a detection apparatus comprising the detection values processing apparatus, a corresponding detection method and a corresponding detection computer program.

BACKGROUND OF THE INVENTION

US 2009/0052621 A1 discloses a computed tomography system comprising an x-ray source for emitting polychromatic radiation, which traverses an examination zone of the computed tomography system. The radiation, which has traversed the examination zone, is detected by a detector for generating energy-dependent detection values. The computed tomography system further comprises a bowtie filter for filtering the radiation before traversing the examination zone. The generated energy-dependent detection values are used for reconstructing an image of the examination zone. The bowtie filter reduces the radiation dose applied to an object, which may be arranged within the examination zone. However, the bowtie filter also adversely affects the detection values such that the quality of the detection values and, thus, of the image reconstructed from the detection values is reduced.

SUMMARY OF THE INVENTION

It is an object of the present invention to provide a detection values processing apparatus, a detection values processing method and a detection values processing computer program, wherein the detection values can be processed such that an image is generated having an improved quality. It is a further object of the present invention to provide a detection apparatus comprising the detection values processing apparatus, a corresponding detection method and a corresponding detection computer program.

In a first aspect of the present invention a detection values processing apparatus is presented, wherein the detection values processing apparatus comprises:
  a detection values providing unit for providing detection values, the detection values being energy-dependent detection values, which are generated by a detector and which are indicative of radiation after having traversed an examination zone, the radiation being polychromatic radiation emitted by a radiation source and being filtered by a filter which comprises K-edge filter material having a K-edge within the energy range of the polychromatic radiation,
  a component decomposition unit for applying a component decomposition technique to the detection values for determining K-edge attenuation values being first component attenuation values, which are indicative of an attenuation caused by the K-edge filter material, and additional component attenuation values, which are indicative of an attenuation caused by additional components of the examination zone, from the energy dependency of the detection values,
  a reconstruction unit for reconstructing an image of the examination zone from the additional component attenuation values.

Since a component decomposition technique is applied to the detection values for determining K-edge attenuation values being first component attenuation values, which are indicative of an attenuation caused by the K-edge filter material, and additional component attenuation values, which are indicative of an attenuation caused by additional components of the examination zone, wherein an image of the examination zone is reconstructed from the additional component attenuation values, an image can be reconstructed, which is less adversely affected by the filter or not at all adversely affected by the filter, because the K-edge attenuation values, which are indicative of attenuations caused by the K-edge filter material of the filter, are not used for reconstructing the image. This improves the quality of the reconstructed image.

The reconstruction unit can be adapted to reconstruct an image of the examination zone from component attenuation values, which correspond to a single additional component, or from component attenuation values, which correspond to several additional components.

The detection values providing unit is preferentially a storage unit, in which the detection values, which have been acquired already, are stored, or a data connection like an Internet connection for providing the detection values to the component decomposition unit via the data connection.

The detection values are preferentially computed tomography projection data, which are generated by moving a polychromatic x-ray source and an examination zone, in which an object to be imaged is preferentially located, relative to each other, wherein polychromatic radiation emitted by the radiation source traverses the examination zone and is detected by an energy-resolving detector. The examination zone is preferentially illuminated by the polychromatic radiation in different angular directions, in order to generate projection data which correspond to different projection directions. Instead of an x-ray radiation source also another radiation source can be used like a nuclear radiation source.

It is preferred that the filter is a bowtie filter, in particular, a dynamically controllable bowtie filter. The bowtie filter is preferentially located between the radiation source and the examination zone. The bowtie filter consists preferentially of two filter parts with varying thicknesses which can be moved dynamically into the x-ray beam from two opposing sides. The thickness of the filter increases towards the outer parts of the beams for reducing the x-ray intensity of the related detector elements. This intensity reduction can compensate for lower attenuation in the peripheral areas of the examination zone which otherwise may cause too high detector radiation. The dynamic bowtie filter can be used to reduce the dynamic range of the radiation intensity over the detector. This reduction can be very helpful, if the detector can operate only in a limited dynamic range such as photon counting detectors with a limited count rate capability.

It is further preferred that the filter is a bowtie filter. The component decomposition unit is preferentially adapted to use at least one of a spatial filter kernel and a temporal filter kernel for smoothing the K-edge attenuation values. It is assumed that the spatial and temporal impact of the filter for filtering the radiation is a smooth function. This means that detection values of neighbored detection elements of the detector as well as temporally successive detections values of the same detection element are assumed to have a similar attenuation contribution from the filter. The filtering of the K-edge attenuation values by using, for example, a spatial filter kernel and/or a temporal filter kernel, can reduce the impact of noise on the K-edge attenuation values and therefore improve the quality of the additional component attenuation values, which are determined while the smoothed K-edge attenuation values, which are less influenced by noise, are given.

The spatial filter kernel and the temporal filter kernel are, for example, average kernels for averaging the K-edge attenuation values for smoothing the same.

The component decomposition unit 13 is preferentially adapted to apply at least one of a base material decomposition technique and a physical effect decomposition technique to the detection values. The component decomposition unit can be adapted to apply a component decomposition technique to the detection values for determining K-edge attenuation values being first component attenuation values, which are indicative of an attenuation caused by the K-edge filter material, and the additional component attenuation values being second component attenuation values, which are indicative of an attenuation caused by a second component, and third component attenuation values, which are indicative of an attenuation caused by a third component, from the energy dependency of the detection values. The reconstruction unit is preferentially adapted to reconstruct an image of the examination zone from a combination of the second component attenuation values and the third component attenuation values. Preferentially, one of the second and third components is a photoelectric effect component of the examination zone for generating photoelectric effect component values and the other of the second and third components is a Compton effect component of the examination zone for generating Compton effect component values.

In an embodiment, the component decomposition unit is adapted for determining the K-edge attenuation values by solving a system of equations for the energy-dependent detection values using a model for the detection values describing an energy-dependent detection value as a combination of a first contribution, which depends on a first energy-dependent attenuation of a first component being the K-edge attenuation of the K-edge filter material, and additional contributions, which depend on additional energy-dependent attenuations by additional components. In particular, the model for the detection values can describe an energy-dependent detection value as a combination of a K-edge contribution, a contribution of a first base material like bone and a further contribution of a further base material like soft tissue. It is also possible that the model for the detection values describes an energy-dependent detection value as a combination of a K-edge contribution, a photoelectric effect contribution and a Compton effect contribution. The component decomposition unit can be adapted for determining the K-edge attenuation values by solving a system of equations for the energy-dependent detection values, using a model for the detection values describing an energy-dependent detection value as a combination of the K-edge effect of the K-edge filter material, the photoelectric effect and the Compton effect, each effect contributing with a corresponding attenuation to the respective energy-dependent detection value. This allows determining K-edge attenuation values, which may be smoothed by using, for example, a spatial filter kernel and/or a temporal filter kernel, effectively in a relatively simple way.

After the K-edge attenuation values have been determined, they can be spatially and/or temporally smoothed, and the smoothed K-edge attenuation values can be used for solving the system of equations for the energy-dependent detection values again, wherein now the smoothed K-edge attenuation values are given and the solution of the system of equations are, for example, photoelectric effect attenuation values and Compton effect attenuation values. The photoelectric effect attenuation values and/or the Compton effect attenuation values can be used for reconstructing an image of the examination zone.

In an embodiment, the component decomposition unit is adapted to correct the photoelectric effect component values and the Compton effect component values with respect to a photoelectric effect and a Compton effect of the filter by a) subtracting from the photoelectric effect component values a product of the corresponding K-edge attenuation values of the K-edge filter material and a provided ratio of photoelectric effect component values of the filter and the K-edge attenuation values of the K-edge filter material and b) subtracting from the Compton effect component values a product of the corresponding K-edge attenuation values of the K-edge filter material and a provided ratio of Compton effect component values of the filter and the K-edge attenuation values of the K-edge filter material. This further reduces possible adverse influence of the filter on the photoelectric effect component values and the Compton effect component values, thereby further improving the quality of an image, which is reconstructed by using the photoelectric effect component values and/or the Compton effect component values.

The component decomposition unit can be adapted to apply the component decomposition technique to the detection values such that further fourth component attenuation values are determined, which are indicative of an attenuation caused by a fourth component being a K-edge examination zone material being a K-edge material in the examination zone, wherein the K-edge of the K-edge examination zone material and the K-edge of the K-edge filter material are different. This allows considering also a K-edge examination zone material within the examination zone like a contrast agent having a K-edge within the energy range of the polychromatic radiation. The fourth component attenuation values are indicative of the K-edge examination zone material and can therefore be reconstructed, separately from the K-edge attenuation values indicative of the attenuation caused by the K-edge filter material, in order to reconstruct an image of the K-edge examination zone material present within the examination zone. Because of the separate reconstruction a negative influence on the reconstruction caused by the filter comprising the K-edge filter material can be reduced, in particular, eliminated. This allows, for example, reconstructing a high quality contrast agent image, if a contrast agent is present in the examination zone.

In a further aspect of the present invention a detection apparatus is presented, wherein the detection apparatus comprises:
  a radiation source for emitting radiation, the radiation being polychromatic radiation, wherein the radiation source is adapted such that the radiation traverses an examination zone of the detection apparatus,
  a detector for generating energy-dependent detection values being indicative of the radiation after having traversed the examination zone,
  a detection values processing apparatus as defined in claim 1.

In a further aspect of the present invention a detection values processing method is presented, wherein the detection values processing method comprises:
  providing detection values, the detection values being energy-dependent detection values, which are generated by a detector and which are indicative of radiation after having traversed an examination zone, the radiation being polychromatic radiation emitted by a radiation source and being filtered by a filter which comprises a K-edge filter material having a K-edge within the energy range of the polychromatic radiation, applying a component decomposition technique to the detection values for determining K-edge attenuation values being first component attenuation values, which are indicative of an attenuation caused by the K-edge filter material, and additional component attenuation values, which are indicative of an attenuation caused by additional components of the examination zone, from the energy dependency of the detection values, reconstructing an image of the examination zone from the additional component attenuation values.

In a further aspect of the present invention a detection method is presented, wherein the detection method comprises:

emitting polychromatic radiation traversing an examination zone, generating energy-dependent detection values being indicative of the radiation after having traversed the examination zone, processing the detection values as defined in claim 12.

In a further aspect of the present invention a detection values processing computer program is presented, wherein the detection values processing computer program comprises program code means for causing a detection values processing apparatus as defined in claim 1 to carry out the steps of the detection values processing method as defined in claim 12, when the detection values processing computer program is run on a computer controlling the detection values processing apparatus.

In a further aspect of the present invention a detection computer program is presented, the detection computer program comprises program code means for causing a detection apparatus as defined in claim 11 to carry out the steps of the detection method as defined in claim 13, when the detection computer program is run on a computer controlling the detection apparatus.

It shall be understood that the detection values processing apparatus of claim 1, the detection apparatus of claim 11, the detection values processing method of claim 12, the detection method of claim 13 and the computer programs of claims 14 and 15 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
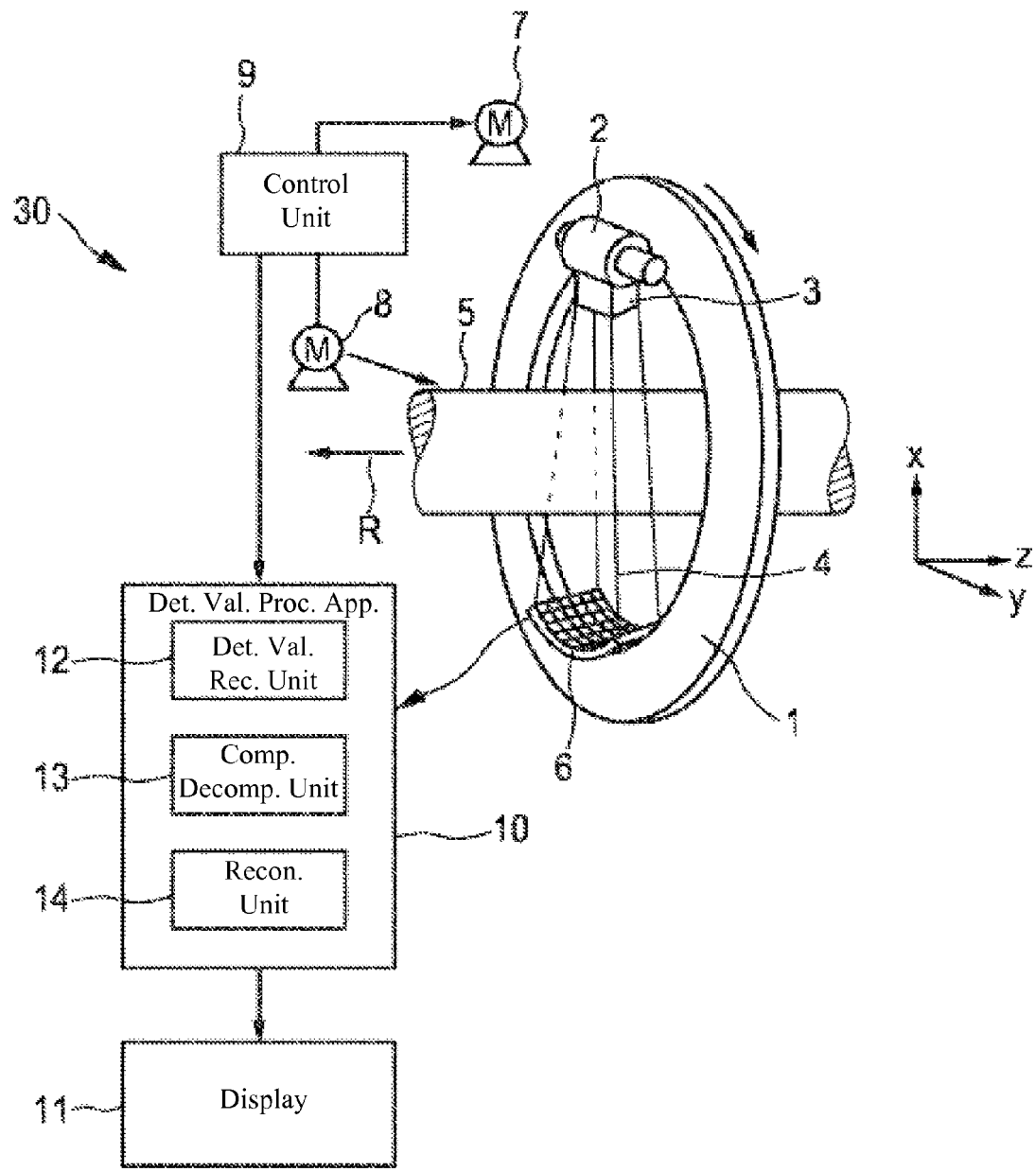
FIG. 1 shows schematically and exemplarily an embodiment of a detection apparatus comprising a detection values processing apparatus.

FIG. 1 shows schematically and exemplarily a detection apparatus being, in this embodiment, a computed tomography system. The computed tomography system 30 includes a gantry 1 which is capable of rotation about a rotational axis R which extends parallel to a z direction. A polychromatic radiation source 2, which is, in this embodiment, an x-ray tube, is mounted on the gantry 1. The radiation source 2 is provided with a collimation and filtering unit 3 for filtering the polychromatic radiation emitted by the radiation source 2 and for forming, in this embodiment, a conical radiation beam 4 from the radiation generated by the radiation source 2. The radiation 4 traverses an object (not shown), such as a patient, in an examination zone 5, which is, in this embodiment, cylindrical. After having traversed the examination zone 5 the radiation beam 4 is incident on an energy-resolving detector 6, which comprises a two-dimensional detection surface. The detector 6 is mounted on the gantry 1.

The energy-resolving detector works, for example, on the principle of counting the incident photons and of outputting detection values that show the number of photons per energy in a certain energy area. Such an energy-resolving detector is, for example, described in the articles Llopart, X., et al., "First test measurements of a 64 k pixel readout chip working in a single photon counting mode", Nucl. Inst. and Meth. A, 509 (1-3): 157-163, 2003 and in Llopart, X., et al., "Medipix2: A 64-k pixel readout chip with 55 mum square elements working in a single photon counting mode", IEEE Trans. Nucl. Sci. 49(5): 2279-2283, 2002, which are herewith incorporated by reference.

Figure 3:
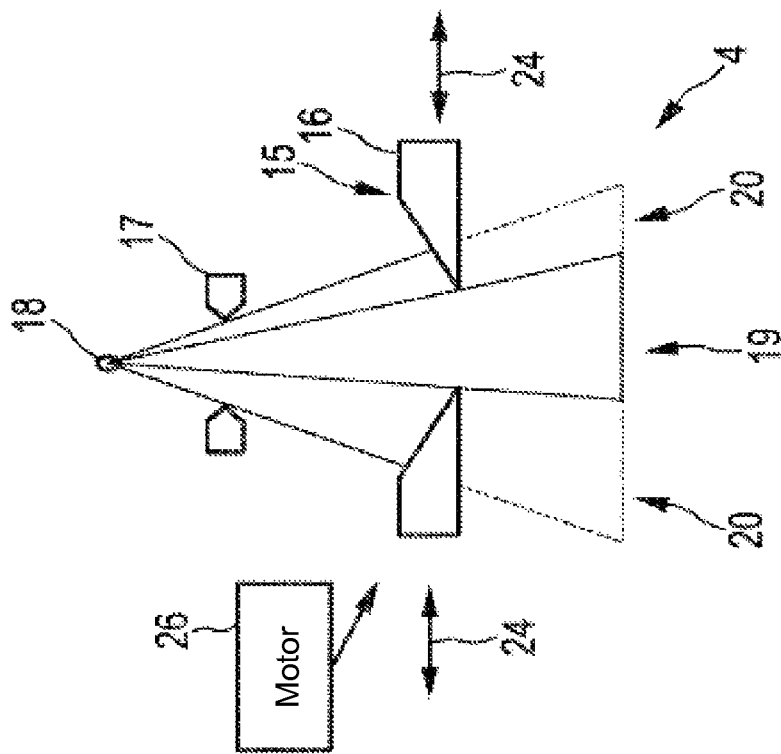
FIGS. 2 and 3 show schematically and exemplarily an embodiment of a bowtie filter.
Figure 2:
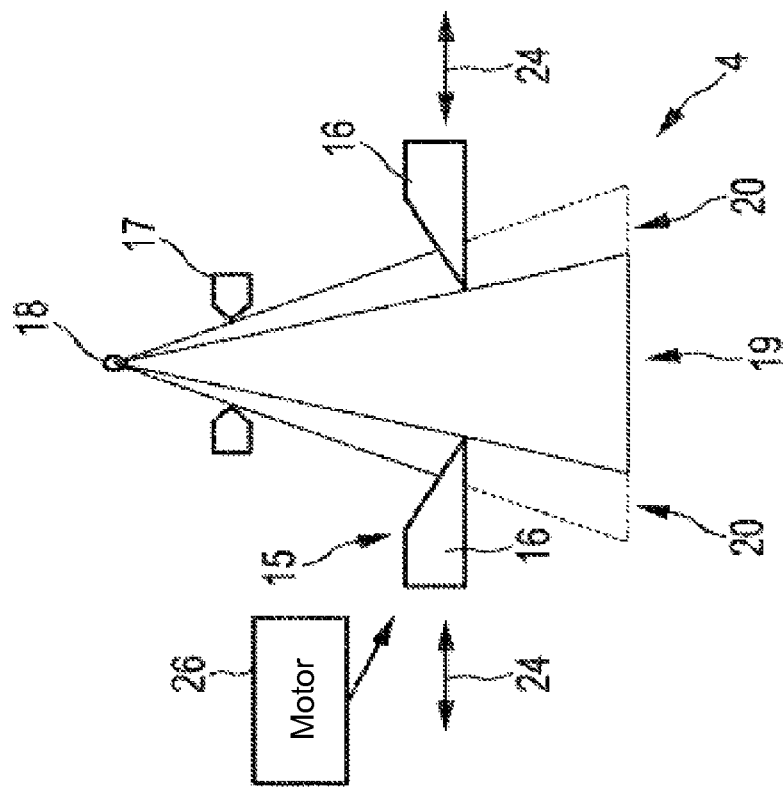

An embodiment of the collimation and filtering unit 3 is schematically and exemplarily shown in FIGS. 2 and 3. The collimation and filtering unit 3 comprises a collimator 17 for collimating the radiation 4 extending from a focal spot 18 and a filter 15 being, in this embodiment, a dynamically controllable bowtie filter. The bowtie filter 15 comprises two parts 16 for attenuating the radiation 4. The resulting radiation 4 comprises a central part 19, which is not filtered by the bowtie filter 15, and peripheral parts 20, which are filtered by the bowtie filter 15. The parts 16 are moveable as indicated by the arrows 24. The parts 16 are preferentially moveable by using a motor 26 which is controlled by the control unit 9. The parts 16 of the bowtie filter 15 have a decreasing thickness towards the center of the radiation. In an embodiment, the parts 16 of the bowtie filter 15 are shaped like corresponding parts of a known stationary bowtie filter, wherein in contrast to the stationary bowtie filter the parts 16 of the dynamically controllable bowtie filter 15 are moveable in the directions indicated by the arrow 24.

In FIG. 2, it is assumed that an object is centrally located within the examination zone 5 and, thus, the dynamically controllable bowtie filter 15 is arranged such that the central part 19 of the radiation 4 is not filtered, but only the peripheral parts 20. FIG. 3 shows an arrangement of the dynamically controllable bowtie filter 15, in which it is assumed that an object is not centrally located within the examination zone 5, wherein the non-attenuated part 19 of the radiation 4 is accordingly shifted off-center.

The filter 15, in particular, the parts 16, comprises K-edge filter material having a K-edge within the energy range of the polychromatic radiation 4. The K-edge filter material comprises atoms having K-edge energies within the energy range of the polychromatic radiation 4. The K-edge filter material comprises, for example, at least one of tantalum, tungsten, gold and lead. One or several of these elements can be used in their metallic state or in another chemical state such as their oxidized state, or they can be used within other stable chemical compounds bearing low Z elements, for example, elements with Z<50. They can be used as a sandwich component with other low atomic number host materials like plastics, low atomic number metals, et cetera or even as a mixture with these host materials. In an embodiment, the energy range of the polychromatic radiation 4 is between about 40 keV and about 110 keV, wherein in this case the atomic numbers Z of the atoms of the K-edge filter material are preferentially in a range from about 56 to about 90.

The computed tomography system comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. These motors 7, 8 are controlled by a control unit 9, for instance, such that the radiation source 2 and the examination zone 5 and, thus, the object within the examination zone 5 move relatively to each other along a helical trajectory. However, it is also possible that the radiation source 2 and the examination zone 5 are moved relatively to each other along another trajectory. For example, the object and the examination zone 5 may not be moved, but only the radiation source 2 may be rotated, i.e. the radiation source 2 may move along a circular trajectory relative to the object or the examination zone 5. Moreover, in another embodiment, the collimation and filtering unit can be adapted for forming another beam shape, in particular, a fan beam, and the detector 6 can comprise a detection surface, which is shaped corresponding to the other beam shape, in particular to the fan beam.

During a relative movement of the radiation source 2 and the examination zone 5 the detector generates energy-dependent detection values depending on the radiation incident on the detection surface of the detector 6.

The detection values which are, in this embodiment, projection data, are transmitted to a detection value processing apparatus 10 via a wired or wireless data connection comprising a detection values receiving unit 12. The detection values receiving unit 12, which may be regarded as being a detection values providing unit, provides the detection values to a component decomposition unit 13 for applying a component decomposition technique to the detection values for determining K-edge attenuation values being first component attenuation values, which are indicative of an attenuation caused by the K-edge filter material, and additional component attenuation values, which are indicative of an attenuation caused by additional components of the examination zone, from the energy dependency of the detection values. The additional component attenuation values are used by a reconstruction unit 14 for reconstructing an image of the object within the examination zone 5 from the additional component attenuation values. For example, the reconstruction unit can be adapted to perform a filtered backprojection, an iterative reconstruction algorithm, an inverse Radon inversion algorithm, et cetera for reconstructing the image from the additional component attenuation values. The reconstructed image can be shown on a display 11.

A K-edge attenuation value corresponds to a line integral of the K-edge absorption coefficients along a ray having caused the respective detection value.

The component decomposition unit can be adapted to smooth the determined K-edge attenuation values and to apply the component decomposition technique again, wherein the additional component attenuation values are determined while the smoothed K-edge attenuation values are given. For smoothing the K-edge attenuation values preferentially a spatial and temporal filter kernel is used. Alternatively, only a spatial filter kernel or a temporal filter kernel can be used. A detection value is preferentially defined by the acquisition time, the energy area, which may also be regarded as being an energy bin, and the detection element of the detector. For spatially smoothing the K-edge attenuation values a K-edge attenuation value related to a certain acquisition time and detection element and can be replaced by an average K-edge attenuation value being the average of K-edge attenuation values related to the certain detection element and detection elements being neighbored to the certain detection element and the same acquisition time. For temporally smoothing the K-edge attenuation values a K-edge attenuation value related to a certain acquisition time and the detection element can be replaced by an average K-edge attenuation value being the average of K-edge attenuation values of the certain acquisition time and neighbored acquisition times, which correspond to the same detection element. In other words, the K-edge attenuations values $A_K^n$ can be smoothed within the temporal spatial neighborhood in the index n, wherein the index n denotes a measurement parameter defined by the respective detection element of the detector 6 and the acquisition time.

In this embodiment, the component decomposition unit 13 is adapted to apply a physical effect decomposition technique to the detection values. However, the component decomposition unit can also be adapted to apply a base material decomposition technique to the detection values. In particular, the component decomposition unit 13 is adapted to apply a component decomposition technique to the detection values for determining K-edge attenuation values being first component attenuation values, which are indicative of an attenuation caused by the K-edge filter material, and additional component attenuation values being second component attenuation values, which are indicative of an attenuation caused by a second component, and third component attenuation values, which are indicative of an attenuation caused by a third component, from the energy dependency of the detection values. The reconstruction unit 14 is then adapted to reconstruct an image of the examination zone from a combination of the second component attenuation values and the third component attenuation values. However, the reconstruction unit 14 can also be adapted to reconstruct an image of the examination zone from the second component attenuation values or the third component attenuation values. The second component is a photoelectric effect component of the examination zone and the third component is a Compton effect component of the examination zone. For determining the K-edge attenuation values and the additional component attenuation values the component decomposition unit is adapted to solve a system of equations for the energy-dependent detection values, wherein a model is used for the detection values describing an energy-dependent detection value as a combination of the K-edge effect of the K-edge filter material, the photoelectric effect and the Compton effect, each effect contributing with a corresponding attenuation to the respective energy-dependent detection value. This system of equations can be, for example, defined as follows:

$$I_b^n = \int S_b(E)\phi(E)e^{-\Sigma_{m \in M} f_m(E) A_m^n} dE, \qquad (1)$$

wherein $I_b^n$ is the respective detection value defined by a measurement parameter n and an energy bin b, wherein the measurement parameter n is defined by the respective detection element of the detector 6 and the acquisition time. The spectral sensitivity within the energy bin b is denoted by $S_b(E)$, the radiation flux from the radiation source 2 is denoted by $\phi(E)$, the different effects like the K-edge effect, the photoelectric effect and the Compton effect, or in other words different components or different contributions, are denoted by m from the set of effects M, the energy-dependent function of the respective effect m, or in other words the energy-dependent attenuation of the respective component m, is denoted by $f_m(E)$, and $A_m^n$ denotes the attenuation values, i.e. the attenuation line integral, of the respective effect m contributing to the detection value defined by the measurement parameter n.

In this embodiment, the number of energy bins is at least three such that the system of equations can be solved with known numerical methods, wherein the quantities $S_b(E)$, $\phi(E)$ and $f_m(E)$ are known and the result of solving the system of equations are the attenuation values $A_C^n$, $A_P^n$ and $A_K^n$ for the Compton effect, the photoelectric effect and the K-edge effect, respectively. The spectral sensitivity $S_b(E)$ and the radiation flux from the radiation source $\phi(E)$ are characteristics of the detection apparatus and are known from, for example, corresponding measurements of the detection apparatus. The energy-dependent functions $f_m(E)$ of the modeled effects are also known from measurements and/or from literature. The reconstruction unit 14 can be adapted to reconstruct a Compton effect image based on the Compton effect attenuation values only, a photoelectric effect image based on the photoelectric effect attenuation values only and/or a combined image based on the photoelectric effect attenuation values and the Compton effect attenuation values, wherein in the latter case preferentially a sum of corresponding photoelectric effect and Compton attenuation values is back projected.

If the bowtie filter 15 comprises not only filter material having a K-edge, but also filter material which contributes significantly to the photoelectric effect and the Compton effect, the component decomposition unit 13 can be adapted to determine the Compton effect attenuation value and the photoelectric effect attenuation value of the bowtie filter 15 and to subtract these filter attenuation values from the photoelectric effect attenuation values $A_P^n$ and the Compton effect attenuation values $A_C^n$ determined in accordance with above mentioned equation (1), in order to correct these attenuation values such that they are not influenced by the bowtie filter. The photoelectric effect of the filter is preferentially determined by multiplying the K-edge attenuation value $A_K^n$ of the K-edge filter material with a provided ratio $R_{KP}$ of the photoelectric attenuation value of the filter and the K-edge attenuation value $A_K^n$ of the K-edge filter material. The Compton effect attenuation value of the filter is preferentially determined by multiplying the K-edge attenuation value $A_K^n$ of the K-edge filter material with a provided ratio $R_{KC}$ of the Compton attenuation value of the filter and the K-edge attenuation value $A_K^n$ of the K-edge filter material. The component decomposition unit 13 can be adapted such that a possible contribution of the bowtie filter 15 to the photoelectric effect and the Compton effect can directly be considered while determining K-edge attenuation values such that simultaneously with determining K-edge attenuation values also the corrected photoelectric effect attenuation values and Compton effect attenuation values are obtained, which are not influenced by the photoelectric effect and the Compton effect of the bowtie filter 15. In particular, the component decomposition unit 13 can be adapted to solve following system of equations:

$$I_b^n = \int S_b(E)\phi(E)e^{-(f_K(E)A_K^n + f_C(E)A_C^N + f_P(E)A_P^n)}dE \text{ with} \quad (2)$$

$$\hat{A}_C^n = A_C^n - R_{KC}A_K^n \text{ and} \quad (3)$$

$$\hat{A}_P^n = A_P^n - R_{KP}A_K^n, \quad (4)$$

wherein $f_C(E)$ denotes an energy-dependent function of the Compton effect and $f_P(E)$ denotes the energy-dependent function of the photoelectric effect. The energy-dependent function of the K-edge material is denoted by $f_K(E)$. Equations (3),(4), $\hat{A}_C^n$ denote the corrected Compton effect attenuation values of the examination zone and $\hat{A}_P^n$ denote the corrected photoelectric effect attenuation values of the examination zone. The reconstruction unit 14 can be adapted to reconstruct an image of the examination zone from the corrected Compton effect attenuation values and/or the corrected photoelectric effect attenuation values.

In an embodiment, the component decomposition unit 13 can be adapted to firstly determine the K-edge attenuation values $A_K^n$ by solving, for example, the equations (1), to smooth the K-edge attenuation values $A_K^n$ for obtaining smoothed K-edge attenuation values $F^n$, and to perform a decomposition technique again, in particular, in accordance with following equation:

$$I_b^n = \int S_b(E)\phi(E)e^{-(f_K(E)F^n + f_C(E)A_C^n + f_P(E)A_P^n)}dE. \quad (5)$$

Moreover, if the bowtie filter 15 does not only comprise the K-edge material, but also contributes to the photoelectric effect and the Compton effect, the component decomposition unit 13 can be adapted to use the smoothed K-edge attenuation values $F^n$ for determining corrected Compton effect attenuation values $\tilde{A}_C^n$ of the examination zone and corrected photoelectric effect attenuation values $\tilde{A}_P^n$ of the examination zone in accordance with following equations:

$$I_b^n = \int S_b(E)(\phi)(E)e^{-(f_K(E)F^n + f_C(E)A_C^n + f_P(E)A_P^n)}dE \text{ with} \quad (6)$$

$$\tilde{A}_C^n = A_C^n - R_{KC}F^n \text{ and} \quad (7)$$

$$\tilde{A}_P^n = A_P^n - R_{KP}F^n. \quad (8)$$

The determined photoelectric effect attenuation values $\tilde{A}_P^n$ and Compton effect attenuation values $\tilde{A}_C^n$ can be used by the reconstruction unit 14 for reconstructing an image of an object present in the examination zone 5.

If in the examination zone 5 a K-edge examination zone material like a contrast agent is present, which has a K-edge, which is different to the K-edge of the K-edge filter material, the component decomposition unit 13 can be adapted to apply the component decomposition technique to the detection values such that further fourth component attenuation values are determined which are indicative of an attenuation caused by a fourth component being the K-edge examination zone material, in particular, in accordance with the following equation:

$$I_b^n = \int S_b(E)\phi(E)e^{-(f_K(E)A_K^n + f_C(E)A_C^n + f_P(E)A_P^n + f_Z(E)A_Z^n)}dE \quad (9)$$

wherein $f_Z(E)$ denotes the energy dependence of the K-edge examination zone material and $A_Z^n$ denotes the first component attenuation values being indicated of the attenuation caused by the K-edge examination zone material. The first component attenuation values are line integrals of the absorption along the respective ray and can be reconstructed by the reconstruction unit 14 for generating an image of the distribution of the K-edge examination zone material within the examination zone 5. For example, if the K-edge examination zone material is a contrast agent within the examination zone, a contrast agent image can be reconstructed.

Figure 4:
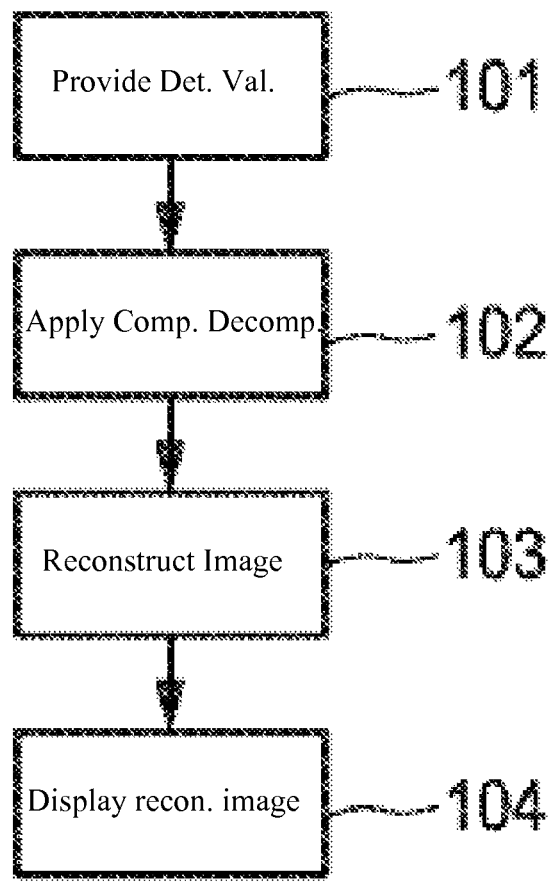
FIG. 4 shows a flowchart exemplarily illustrating an embodiment of a detection values processing method.

In the following an embodiment of a detection value processing method is exemplarily described with reference to a flowchart shown in FIG. 4.

In step 101, detection values are provided. The detection values are energy-dependent detection values, which are generated by the detector 6 and which are indicative of the radiation 4 after having traversed the examination zone 5. The radiation 4 is polychromatic radiation emitted by the radiation source 2 and is filtered by the bowtie filter 15 which comprises a K-edge filter material having a K-edge within the energy range of the polychromatic radiation 4. In step 102, a component decomposition technique is applied to the detection values for determining K-edge attenuation values being first component attenuation values, which are indicative of an attenuation caused by the K-edge filter material, and additional component attenuation values, which are indicative of an attenuation caused by additional components of the examination zone, from the energy-dependency of the detection values. In step 103, an image of the examination zone is reconstructed from the additional component attenuation values. For example, in step 102 Compton effect attenuation values and photoelectric effect attenuation values can be determined, and, in step 103, the Compton effect attenuation values and/or the photoelectric effect attenuation values can be used for reconstructing an image of the examination zone. In step 104, the reconstruction image is shown on the display 11.

Figure 5:
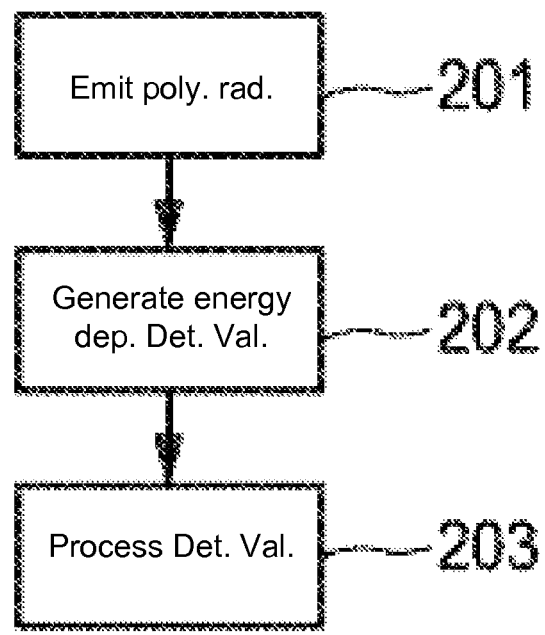
FIG. 5 shows a flowchart exemplarily illustrating an embodiment of a detection method.

FIG. 5 shows exemplarily a flowchart illustrating an embodiment of a detection method. In step 201, the radiation source 2 emits polychromatic radiation 4 traversing the examination zone 5 and, in step 202, energy-dependent detection values are generated by the detector 6, wherein the detection values are indicative of the radiation 4 after having traversed the examination zone 5. In step 203, the detection values are processed as described above with reference to FIG. 4.

If a dynamically controlled bowtie filter is used for photon counting computed tomography as described above, the main difficulty is generally the calibration of the bowtie filter. In difference to a static bowtie filter, where the impact of the filter on the measurement can simply be measured with a calibration scan, the dynamic bowtie filter changes the attenuation for, in particular, every detector pixel, i.e. every detector element, dynamically during a scan of the object, which may be a patient. However, a precise knowledge of the impact of the bowtie filter should be available for every detector element and every projection measurement, in order to correct the detection values for the influences by the bowtie filter.

The dynamic bowtie filter is made from a filter material that contains atoms that can be detected with K-edge imaging which allows selective and quantitative imaging of specific atoms using, for example, energy selective detectors such as photon counting detectors with energy separation. The dynamic bowtie filter is made of or contains a well defined concentration of such a K-edge material. Therefore, the attenuation from the bowtie filter can easily be determined from the detection values.

Since the attenuation by the bowtie filter can be determined, processing and calibration can become simple. For example, the scanner, i.e. the detection apparatus, can be calibrated as usual without any bowtie filtration in the beam, wherein each scan can be corrected with the pre-acquired calibration information as usual. For each detector reading a material decomposition can be done. The base materials for the decomposition have to include the K-edge material of the bowtie material. This is directly the attenuation caused by the bowtie filter K-edge material. If the bowtie material is a mixture of the K-edge material and other components, the attenuation of these components, for example, of a photoelectric effect component and a Compton effect component, can be estimated given the well-known composition of the bowtie material.

The above described projection domain component decomposition estimates $A_m^n$ given the measurement and the above described model of the measurement as defined in, for example, equation (1). If the bowtie filter material contains the K-edge element, the component decomposition delivers the related attenuation integral $A_K^n$. Since the bowtie filter K-edge material has its own component base, it does not contaminate the other base components and is separated into a separate kind of channel. If the bowtie filter material is a mixture of the K-edge material and other components, a known relative concentration and the known spectral absorption of the other components can be used to correct the other base component integrals. For example, the additional components in the bowtie filter can be properly modeled with their Compton and photoelectric absorption as described above.

An initial component decomposition with the corrected Compton and photoelectric effect component can directly be used as output, because the bowtie filter impact is subtracted from the results as described above with reference to, for example, equations (2) to (4). In another embodiment, the component decomposition can be repeated with a modified model in which the then known smoothed K-edge attenuation values $F^n$ are used as described above with reference to, for example, equations (5) to (8).

Although in the above described embodiments the different components are, besides the K-edge component, a photoelectric effect component and a Compton effect component, the different components can also represent different base materials. Moreover, although in the above described embodiments three components are preferentially modeled, the detection value processing apparatus can also be adapted to model more than three different components.

The above mentioned equations can be combined. For example, also in equation (9) already determined and smoothed K-edge attenuation values can be used. Moreover, also with respect to equation (9) the correction of the photoelectric effect component attenuation values and Compton effect attenuation values as defined by equations (3), (4) and (7), (8) can be used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of the K-edge attenuation values and the additional component attenuation values performed by one or several units can be performed by any other number of units or devices. For example, steps 102 and 103 can be performed by a single unit or by any other number of different units. The calculations and/or the control of the detection values processing apparatus in accordance with the detection values processing method and/or the control of the detection apparatus in accordance with the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detection values processing apparatus. Energy-dependent detection values are provided, which are indicative of polychromatic radiation after having traversed an examination zone. The radiation is filtered by a filter which comprises K-edge filter material. A component decomposition technique is applied to the detection values for determining K-edge attenuation values being first component attenuation values, which are indicative of an attenuation caused by the K-edge filter material, and additional component attenuation values, which are indicative of an attenuation caused by additional components of the examination zone, wherein an image of the examination zone is reconstructed from the additional component attenuation values. An image can therefore be reconstructed, which is not adversely affected by the filter, because the K-edge attenuation values are not used for reconstructing the image. This can improve the quality of the reconstructed image.

The invention claimed is:

1. A detection values processing apparatus, the detection values processing apparatus comprising: a computer comprising: one or more processors and a memory communicatively coupled to the one or more processors and the memory storing instructions comprising:
   a detection values providing unit configured to provide energy-dependent detection values, which are generated by a detector indicative of polychromatic radiation emitted by a radiation source, filtered by a filter which comprises K-edge filter material having a K-edge within the energy range of the polychromatic radiation, having traversed an examination zone, and detected by the detector;
   a component decomposition unit configured to apply a component decomposition technique to the energy-dependent detection values which determine K-edge attenuation values, and the determined K-edge attenuation values include first component attenuation values indicative of an attenuation caused by the K-edge filter material, and additional component attenuation values indicative of an attenuation caused by additional components of the examination zone;
   a reconstruction unit configured to reconstruct an image of the examination zone from the additional component attenuation values;
   wherein the additional component attenuation values include second component attenuation values indicative of an attenuation caused by photoelectric effect, and third component attenuation values indicative of an attenuation caused by Compton effect; and
   wherein the component decomposition unit corrects the photoelectric effect component values by subtracting from the second component attenuation values, a product of the corresponding K-edge attenuation values of the K-edge filter material and a ratio of second component attenuation values of the filter and the K-edge attenuation values of the K-edge filter material, and corrects the Compton effect component values by subtracting from the third component attenuation values, a product of the corresponding K-edge attenuation values of the K-edge filter material and a ratio of the third component attenuation values of the filter and the K-edge attenuation values of the K-edge filter material.

2. The detection values processing apparatus as defined in claim 1, wherein the filter is a bowtie filter comprising at least one of tantalum, tungsten, gold or lead.

3. The detection values processing apparatus as defined in claim 1, wherein the filter is a dynamically controllable bowtie filter.

4. The detection values processing apparatus as defined in claim 1, wherein the component decomposition unit smooths the determined K-edge attenuation values and reapplies the component decomposition technique.

5. The detection values processing apparatus as defined in claim 4, wherein the component decomposition unit smooths the K-edge attenuation values using at least one of a spatial filter kernel and a temporal filter kernel.

6. The detection values processing apparatus as defined in claim 1, wherein the reconstruction unit reconstructs the image of the examination zone from a combination of the second component attenuation values and the third component attenuation values.

7. The detection values processing apparatus as defined in claim 1, wherein the additional component attenuation values include fourth component attenuation values indicative of an attenuation caused by a K-edge material in the examination zone, and a K-edge of the K-edge examination zone material and the K-edge of the K-edge filter material are different.

8. A detection apparatus, the detection apparatus comprising:
   a radiation source configured to emit polychromatic radiation traversing an examination zone of the detection apparatus;
   a filter comprising K-edge filter material having a K-edge within the energy range of the polychromatic radiation;
   a detector configured to generate energy-dependent detection values indicative of the polychromatic radiation after having traversed the examination zone, and the detection values processing apparatus as defined in claim 1.

9. A detection values processing method, the detection values processing method comprising:
   providing energy-dependent detection values generated by a detector and indicative of polychromatic radiation after having traversed an examination zone, emitted by a radiation source, and filtered by a filter which comprises a K-edge filter material having a K-edge within the energy range of the polychromatic radiation;
   applying a component decomposition technique to the energy-dependent detection values which determines K-edge attenuation values including first component attenuation values indicative of an attenuation caused by the K-edge filter material, and additional component attenuation values indicative of an attenuation caused by additional components of the examination zone; and
   reconstructing an image of the examination zone from the additional component attenuation values;
   wherein the additional component attenuation values include second component attenuation values indicative of an attenuation caused by photoelectric effect, and third component attenuation values indicative of an attenuation caused by Compton effect; and
   wherein applying a component decomposition technique includes correcting the photoelectric effect component values by subtracting from the second component attenuation values, a product of the corresponding K-edge attenuation values of the K-edge filter material and a ratio of second component attenuation values of the filter and the K-edge attenuation values of the K-edge filter material, and correcting the Compton effect component values by subtracting from the third component attenuation values, a product of the corresponding K-edge attenuation values of the K-edge filter material and a ratio of the third component attenuation values of the filter and the K-edge attenuation values of the K-edge filter material.

10. The method according to claim 9, further comprising:
emitting polychromatic radiation;
filtering the emitted radiation with the filter comprising the K-edge filter material; and
detecting the polychromatic radiation having traversed an examination zone and generating energy-dependent detection values indicative of the detected polychromatic radiation.

11. A detection values processing computer program, the detection values processing computer program comprising a non-transitory storage medium of program code for causing a computer to carry out the steps of the detection values processing method of claim 9.

12. The method according to claim 9, wherein the filter is a dynamically controllable bowtie filter comprising at least one of tantalum, tungsten, gold or lead.

13. The method according to claim 9, wherein the additional component attenuation values include an attenuation component indicative of a K-edge contrast material disposed in the examination region, and a K-edge of the K-edge contrast material is different from the K-edge of the K-edge filter material.

14. The method according to claim 13, wherein reconstructing includes reconstructing using the attenuation component indicative of the K-edge contrast material disposed in the examination region, and without the first attenuation values indicative of the attenuation caused by the K-edge filter material.

15. The method according to claim 14, further including:
displaying the reconstructed image on a display device, and the reconstructed image includes a contrast agent image.

* * * * *